United States Patent [19]

Hlavka

[11] Patent Number: 5,743,880
[45] Date of Patent: Apr. 28, 1998

[54] SIDE LOAD TOLERANT INSTRUMENTS FOR USE IN LAPAROSCOPIC SURGERY

[75] Inventor: Edwin J. Hlavka, Palo Alto, Calif.

[73] Assignee: Origin Medsystems, Inc., Menlo Park, Calif.

[21] Appl. No.: 455,293

[22] Filed: May 31, 1995

Related U.S. Application Data

[63] Continuation of Ser. No. 994,124, Dec. 21, 1992, abandoned.

[51] Int. Cl.$^6$ ................................. A61M 27/00
[52] U.S. Cl. ..................... 604/164; 604/264; 604/280; 606/167
[58] Field of Search ........................ 606/167, 170, 606/185; 604/164, 165, 264, 272, 280

[56] References Cited

U.S. PATENT DOCUMENTS

| | | | |
|---|---|---|---|
| 3,833,003 | 9/1974 | Taricco | 604/164 |
| 4,654,030 | 3/1987 | Moll et al. | 606/185 |
| 4,863,430 | 9/1989 | Klyce et al. | 604/164 |
| 4,976,684 | 12/1990 | Broadnax, Jr. | 604/272 |
| 5,013,292 | 5/1991 | Lemay | 606/232 |
| 5,215,526 | 6/1993 | Deniega et al. | 606/185 |

Primary Examiner—Michael Peffley
Attorney, Agent, or Firm—Limbach & Limbach LLP

[57] ABSTRACT

A side-load tolerant instrument, comprising an outer part and an inner part, for use in laparoscopic procedures in a body cavity. The inner part is elongate and includes a housed portion, which is part of the length of the inner part. The outer part is elongate, houses the housed portion of the inner part, and permits the housed portion to move freely axially relative to it. The outer part bends lengthways when an external side load is applied to it. The outer part exerts an internal side load on the housed portion of the inner part to bend the housed portion lengthways to conform to the lengthways bending of the outer part. Side-load tolerance is provided by reducing the internal side load between outer part and the inner part resulting from the outer part bending lengthways in response to the external side load. The reduced internal side load reduces friction between the outer part and the inner part when the instrument is subject to the external side load. The inner part includes a lateral compliance device that reduces the internal side load required to bend the housed portion of the inner part to conform to lengthways bending of the outer part. Alternatively, the housed portion of the inner part may be shaped over at least part of its length to accommodate a laterally-displaced portion of the outer part that results from the lengthways bending of the outer part.

18 Claims, 5 Drawing Sheets

SIDE LOAD TOLERANT INSTRUMENTS FOR USE IN LAPAROSCOPIC SURGERY

This is a continuation of application Ser. No. 07/994,124 filed on 21 Dec. 1992 (now abandoned).

BACKGROUND OF THE INVENTION

Instruments for use in laparoscopic surgery are generally elongate and are adapted to provide a gas-tight seal with a trocar robe or with a puncture in the body wall. Many laparoscopic instruments such as trocar assemblies, clip appliers and forceps, have two main parts passing through the body wall, an outer, static part, and an inner part mounted inside the outer part. The inner part is capable of sliding axially or rotating relative to the outer part.

Under normal conditions, the inner part freely slides axially or rotates relative to the outer part. However, in certain procedures, the surgeon applies a transverse manipulating force (a "side load") to the proximal part of the instrument against a reaction applied to the distal part of the instrument provided by the body part being manipulated by the instrument. The side load causes the instrument to bend along its long axis, i.e., lengthways, which gives rise to lateral forces between the inner part of the instrument and the outer part. Friction resulting from the lateral forces partially or totally impairs the ability of the inner part to slide axially or to rotate relative to the outer part, and renders the instrument partially or wholly inoperative.

The consequences of inoperability due to side loads can be particularly severe in self-shielding trocar assemblies. A trocar assembly consists of a trocar (inner part) mounted inside the bore of a trocar robe (outer part). The trocar assembly is thrust through a body cavity wall, normally the abdominal wall, to form a puncture. The trocar is then withdrawn from the trocar tube, and laparoscopic instruments are inserted into the body cavity through the trocar tube.

The trocar includes a sharp, elongate trocar tip mounted on the distal end of an elongate obturator. The trocar of the trocar assembly is preferably self shielding to prevent the trocar tip, after it has penetrated through body cavity wall, from injuring underlying organs or tissues. The trocar tip penetrating through the body cavity wall causes a shield to spring distally to cover the trocar tip, or causes the trocar tip to spring proximally back into the trocar tube. Either way, the organs or tissue underlying the body cavity wall are protected from the trocar tip.

It has been customary to drive the trocar assembly through the body cavity wall in a direction normal to the body cavity wall. Any side loads on the trocar assembly resulting from this procedure are below the threshold that impairs the operation of the self-shielding mechanism. More recently, angled driving techniques have been developed, especially for penetrating the abdominal wall in obese and morbidly obese patients. In the "Z-technique," the trocar assembly is initially driven in a direction normal to the abdominal wall. After the trocar tip has been driven in a short distance, the surgeon applies a torque to the proximal part of the trocar assembly to change the angle between the trocar assembly and the abdominal wall. While applying the torque, the surgeon then drives the trocar assembly through the abdominal wall at an oblique angle. This technique is intended to reduce the risk of the trocar tip injuring underlying organs, but results in severe side loads being applied to the trocar assembly.

The side loads resulting from the Z-technique can be sufficiently high to cause the self-shielding mechanism of known trocar assemblies to malfunction. The self-shielding mechanism trips when the trocar tip penetrates the abdominal wall, but friction resulting from lateral forces between the trocar and the trocar tube as a result of the trocar assembly bending when subject to a side load prevents the shield from moving distally to cover the trocar tip, or prevents the trocar tip from moving proximally back into the trocar tube. The trocar tip enters the abdominal cavity unshielded, with the potential to injure underlying organs or tissue, or adjacent abdominal wall.

It has been suggested to reduce the tendency of the self-shielding mechanism of a trocar assembly to malfunction when the trocar assembly is subject to a side load by increasing the force of the spring driving the mechanism. It has been found that this approach results in the self-shielding mechanism tripping prematurely. Moreover, this approach cannot be used in instruments in which the mechanism subject to jamming is not spring driven.

It has also been suggested to stiffen the trocar assembly to reduce bending as a result of side loads. This approach is incompatible with the trend to minimizing the outside diameter of laparoscopic instruments to reduce the size of punctures required.

OBJECTS AND SUMMARY OF THE INVENTION

It is an object of the invention to provide a two-part laparoscopic instrument in which impairment of the movement of the inner part when the instrument is subject to a side load is reduced or avoided.

It is a further object of the invention to provide a two-part laparoscopic instrument in which the inner part can transmit a substantial axial force without its movement being impaired when the instrument is subject to a side load.

It is a further object of the invention to provide a two-part laparoscopic instrument that can undergo significant lengthways bending in response to a side load without the movement of the inner part being impaired.

It is a further object of the invention to provide a trocar assembly in which impairment of the axial movement of the self-shielding mechanism is reduced or avoided when the trocar assembly is subject to a side load.

It is a further object of the invention to provide a trocar assembly in which the obturator can transmit a substantial axial force to the trocar tip without the axial movement of the trocar tip being impaired when the trocar assembly is subject to a side load.

It is a further object of the invention to provide a trocar assembly in which the assembly can undergo significant lengthways bending in response to a side load without the axial movement of the trocar tip being impaired.

It is a further object of the invention to provide a trocar assembly in which the obturator passes through a housing, and can slide freely through the housing when the trocar assembly is subject to a side load.

It is a further object of the invention to provide a trocar assembly in which the trocar tube includes a rear door, and the obturator can slide freely through the rear door when the trocar assembly is subject to a side load.

It is a further object of the invention to provide a trocar assembly in which the trocar tip is articulated relative to the obturator.

It is a further object of the invention to provide a trocar assembly in which the obturator is flexible enough to allow the trocar assembly to undergo significant lengthways bending in response to a side load without the axial movement of the trocar tip being impaired.

Accordingly, the invention provides a side-load tolerant instrument, comprising an elongate outer part and an elongate inner part, for use in laparoscopic procedures in a body cavity. The outer part bends lengthways when subject to a side load. The inner part is movable within the outer part, and bends lengthways in response to a lateral force. The inner portion includes a lateral compliance device that reduces the lateral force required to bend the inner part lengthways to conform to the lengthways bending of the outer part.

A side load causes lengthways bending of the outer part, which causes the outer part to exert a lateral force against the inner part. Friction resulting from the lateral force impairs movement of the inner part. The lateral compliance device reduces the lateral force and the resulting friction between the inner part and the outer part. This avoids or reduces impairment of the movement of the inner part.

The present invention additionally provides a side-load tolerant instrument, comprising an elongate outer part and an elongate inner part, for use in laparoscopic procedures in a body cavity. The outer part bends lengthways when subject to a side load, and a portion of the outer part is laterally displaced as a result of the lengthways bending. The inner part moves within the outer part, and is shaped over at least part of its length to accommodate the laterally displaced portion of the outer part when the outer part is subject to a side load.

A side load causes lengthways bending of the outer part. This causes a portion of the outer part that is laterally displaced as a result of the bending to contact the inner part, and to exert a lateral force thereon. Friction resulting from the lateral force impairs the movement of the inner part. By shaping the inner part to accommodate the laterally-displaced portion of the outer part, contact between the inner part and the laterally-displaced portion of the outer part is avoided or reduced. Consequently, the lateral force and the resulting friction between the inner part and the outer part are reduced, which avoids or reduces impairment of the movement of the inner part.

The present invention also provides a side-load tolerant trocar assembly comprising a substantially elongate trocar tube and a substantially elongate trocar. The trocar tube bends lengthways when subject to a side load. The trocar is axially movable within the trocar tube, and bends lengthways in response to a lateral force. The trocar includes a lateral compliance device that reduces the lateral force required to bend the trocar lengthways to conform to the lengthways bending of the trocar tube.

Finally, the present invention provides a side-load tolerant trocar assembly comprising a trocar tube and a trocar. The trocar tube bends lengthways when subject to a side load, and a portion of the trocar tube is laterally displaced as a result of the lengthways bending. The trocar is axially movable within the trocar tube, and is shaped over at least part of its length to accommodate the laterally-displaced portion of the trocar tube when the trocar tube is subject to a side load.

DETAILED DESCRIPTION OF THE INVENTION

A self-shielding trocar assembly to which the present invention can be applied will first be described with reference to FIGS. 1A through 1C. This description is for illustrative purposes only, and is not intended to imply any limit to the applicability of the invention. The invention can easily be adapted to work in other two-component laparoscopic instruments.

The trocar assembly 10 comprises the trocar 11 and the trocar tube 14. FIG. 1A shows the trocar assembly in its normal state, and FIG. 1B shows the trocar assembly with the trocar tip 12 withdrawn into the trocar tube 14 after the self-shielding mechanism (not shown) has operated.

The trocar 11 comprises the trocar tip 12, the obturator 16, and the rear housing 30. The trocar tip 12 forms a linear extension of the obturator 16, and can rotate relative to the obturator. The trocar tip 12 is made of surgical steel, and its distal end is ground to provide a faceted piercing portion 18, with the sharp point 20, and the sharp cutting edges 22. The obturator 16 is an elongate, rigid, stainless steel shaft with a distal portion 26 having a diameter substantially equal to that of the trocar tip 12.

The proximal portion 24 of the obturator 16 has a reduced diameter compared with the distal portion 26 and passes through the bush 28 into the rear housing 30. The surgeon holds the trocar assembly 10 using the rear housing, and applies most of the axial and transverse manipulating forces to the trocar assembly via the rear housing.

The self-shielding mechanism (not shown) is located in the rear housing 30. Pressing the palm button 32 on the proximal end of the rear housing advances the proximal part 24 of the obturator from the position shown in FIG. 1B to the position shown in FIG. 1A, and locks the obturator in the position shown in FIG. 1A. This causes the trocar tip 12 to project out of the cannula 15, as shown in FIG. 1A.

The self-shielding mechanism is cocked by applying an axial force greater than a first threshold value to the trocar tip 12. The axial force is directed towards the rear housing 30, and would normally be applied by driving the trocar tip into the abdominal wall. Thereafter, if the axial force applied to the trocar tip falls below a second threshold value, such as would occur when the trocar tip penetrates through the abdominal wall into the abdomen, the self-shielding mechanism rapidly retracts the proximal part 24 of the obturator back into the rear housing, as shown in FIG. 1B. This retracts the trocar tip 12 into the position shown in FIG. 1B, where it is shielded by the cannula 15.

The trocar tube 14 includes the valve body 34 and the cannula 15. The cannula 15 has a gradually tapering bore, the diameter of which reduces in the direction distal from the valve body. The distal-most part of the cannula has a diameter that provides a sliding fit with the trocar tip 12. The wall thickness of the cannula 15 is substantially constant over most of the length of the cannula, but is reduced towards the distal end to help the distal end 17 of the cannula to penetrate the puncture formed in the body cavity wall by the trocar tip.

The body cavity in which the trocar assembly 10 is used is normally insufflated before the trocar assembly is driven through the body cavity wall. Insufflation provides a clearance between the body cavity wall and the underlying organs and tissues, and reduces the possibility of the trocar tip 12 injuring the underlying organs and tissues after it has penetrated through the body cavity wall. To preserve the insufflated body cavity, the trocar tube 14 includes the valve body 34.

The valve body 34 includes the diaphragm seal 36 which forms a gas-tight seal with the proximal part 24 of the obturator. The gas-tight seal between the diaphragm seal and the obturator prevents insufflation gas passing between the cannula 15 and the trocar tip 12 from escaping. The diaphragm seal can also form a gas-tight seal with other instruments passed into the body cavity through the trocar tube 14 after the trocar 11 has been withdrawn.

The diaphragm seal 36 also includes the peripheral lip 38 with which the spring-loaded, hinged door 40 forms a gas-tight seal when no trocar 11 or other instrument is present in the trocar tube 14.

Figure 2A:
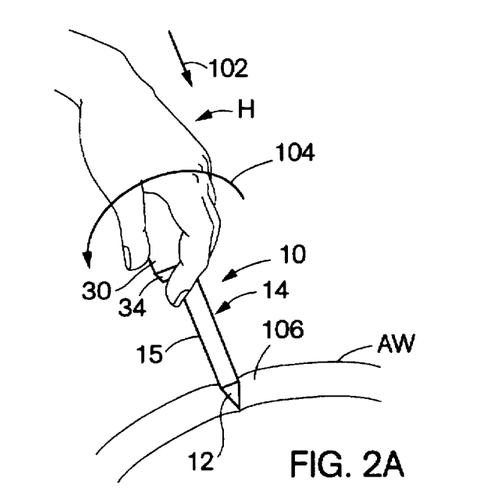
FIG. 2A shows how a side load is applied to a trocar assembly

FIG. 2A shows the trocar assembly 10 being driven into the insufflated abdominal wall AW. The trocar is held with the rear housing 30 nested in the surgeon's hand H. The surgeon's fingers and thumb contact the rear housing and part of the valve body 34.

Pressure between the palm of the surgeon's hand H and the proximal portion of the rear housing 30 provides an axial force that drives the trocar tip 12 and the distal part of the cannula 15 through the abdominal wall in the direction shown by the arrow 102. In addition, the surgeon is shown changing the direction in which the trocar tip is driven by exerting a torque in the direction indicated by the arrow 104. The abdominal wall resists the torque with a transverse force indicated by the arrow 106. The resulting side load on the trocar assembly 10 causes the cannula 15 to bend lengthways.

Figure 1A:
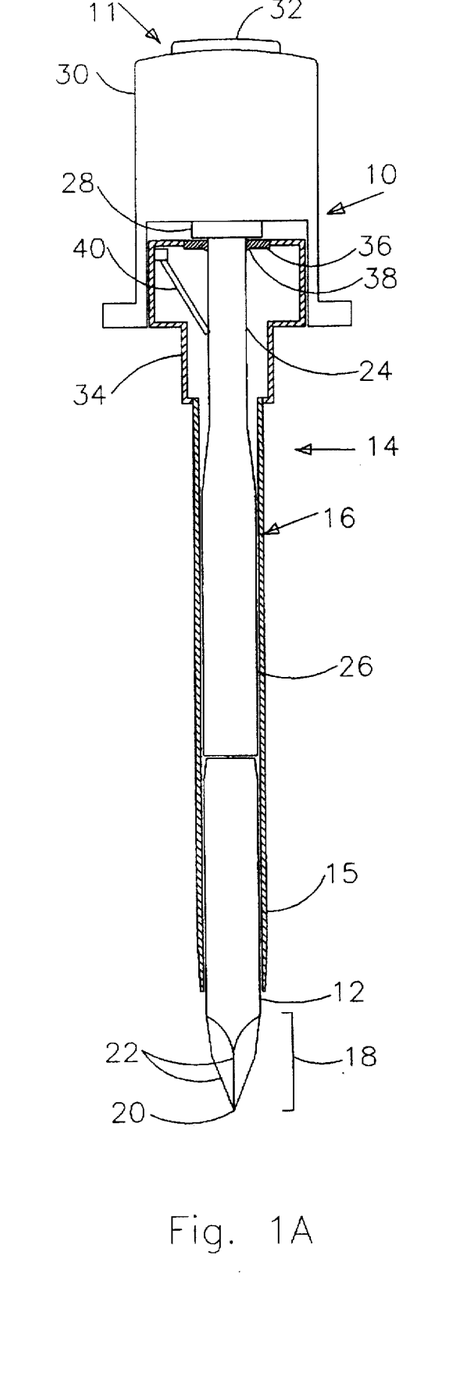
FIG. 1A shows a trocar assembly with the trocar tip in its normal position.
Figure 1B:
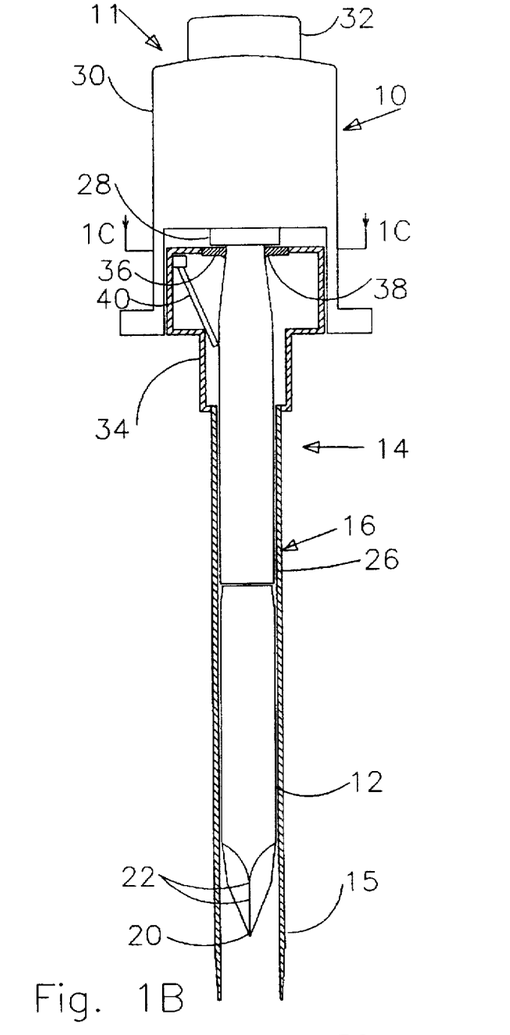
FIG. 1B shows a trocar assembly after the self-shielding mechanism has operated.
Figure 1C:
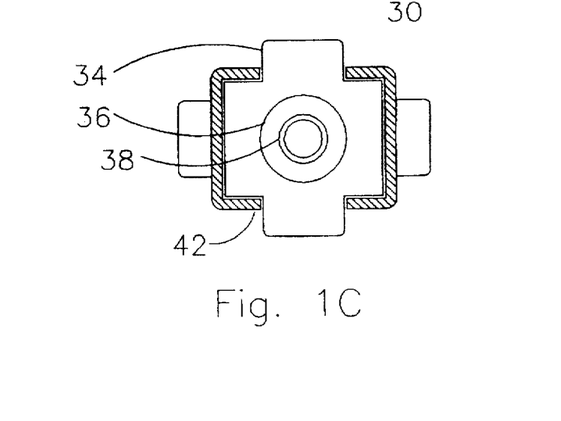
FIG. 1C is a cross sectional view of the trocar assembly shown in FIG. 1B.

The valve body 34 is shaped as shown in FIGS. 1A through 1C so that it interlocks with flanges, e.g., the flange 42, on the rear housing 30. The interlocking of the valve body and the rear housing enables the manipulating forces to be transferred from the rear housing to the valve body, and thence to the cannula 15, when the trocar assembly 10 is driven through the body cavity wall.

The valve body 34 and the rear housing 30 do not form a perfectly integral unit, however, and can pivot about one another. Thus, in addition to the cannula 15 bending lengthways, the trocar assembly as a whole bends lengthways as the rear housing 30 pivots relative to the valve body 34.

Figures 2B, 2C:
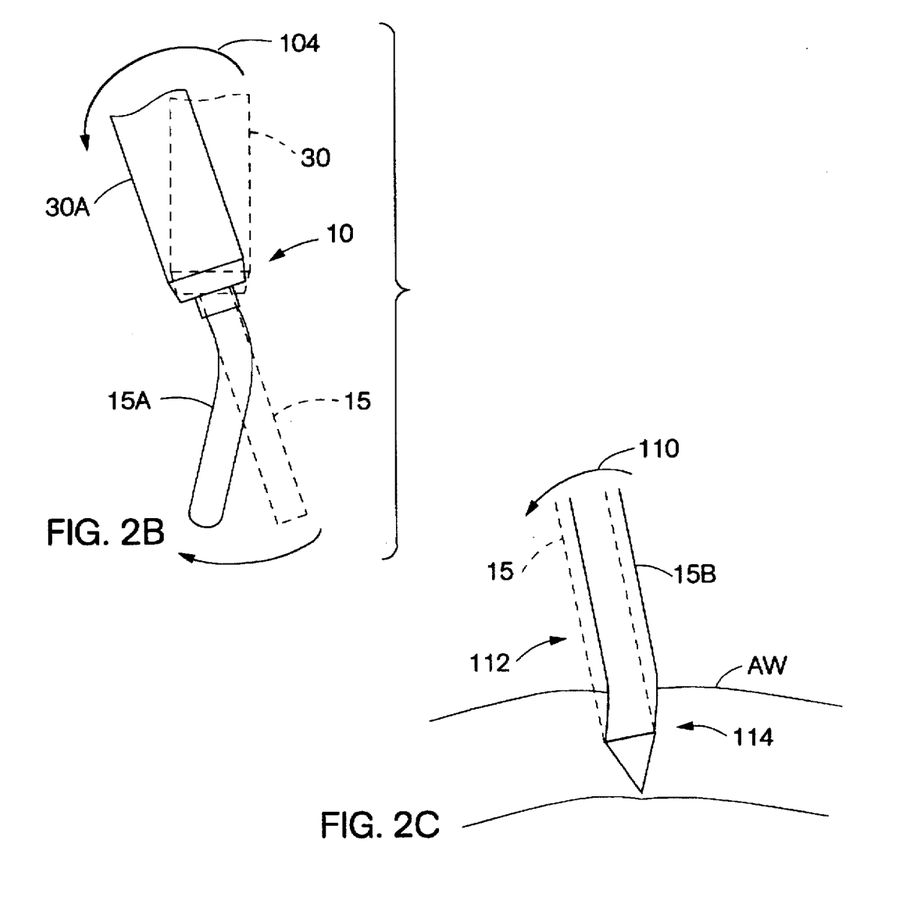
FIG. 2B shows a side load causes bending of the cannula and of the trocar assembly.
FIG. 2C shows how a localized side load causes localized bending of the cannula.

FIG. 2B also shows an exaggerated view of the how the trocar assembly 10 bends lengthways as a result of a side load. The side load causes the cannula to bend from the shape indicated by the reference numeral 15 to the shape indicated by the reference numeral 15A, and causes the rear housing 30 to pivot relative to the valve body 34 (and the cannula 15) from its normal position indicated by the reference numeral 30 to the position indicated by the reference numeral 30A.

There can also be some localized bending of the cannula 15 as shown in FIG. 2C. Localized bending results from the abdominal wall exerting transverse forces 112 and 114 in opposite directions in response to moving the rear housing (not shown) in the direction indicated by the arrow 110. This causes lengthways bending over a relatively short extent of the cannula near its distal end, as indicated by the reference numeral 15B.

The bending of the trocar assembly 10 as a whole, and of the housing to the valve body, and thence to the cannula 15, when the cannula 15, misaligns the trocar 11 relative to the trocar tube 14, and gives rise to lateral forces between the cannula 15 and trocar tip 12 and the obturator 16. The bending also gives rise to lateral forces between the obturator 16 and the diaphragm seal 36 and the bush 28 in the rear housing. Friction resulting from the lateral forces opposes the longitudinal force exerted by the self-shielding mechanism and, if high enough, prevents the self-shielding mechanism from retracting the trocar tip.

In other laparoscopic instruments, applying a side load causes the outer part of the instrument to bend, which results in a lateral force between the outer part and the inner part. Friction resulting from the lateral force between the outer part and the inner part partially or totally impairs the ability of the inner part to move relative to the outer part, and hence impairs the operability of the instrument.

To overcome this problem, an instrument according to a first aspect of the invention includes an inner part that has lateral compliance, so that it can bend lengthways in response to the bending of the outer part of the instrument caused by the side load. Compared with a normal inner part without lateral compliance, using an inner part with lateral compliance reduces the lateral force required to bend the inner part to conform to the bending of the outer part. This reduces the lateral force between the inner part and the outer part, which, in turn, reduces the frictional force between the inner and outer parts. The reliability of the instrument is improved. Additionally or alternatively, the amount of side load that the instrument can tolerate before its operability is impaired can be significantly increased.

An instrument according to the second aspect of the invention includes an inner part that is shaped such that the outer part can bend in response to a side load without contacting the shaped inner part or with reduced contact with the shaped inner part. With such an arrangement, the outer part bends under a side load, and the inner part accommodates the laterally-displaced part of the outer part caused by the bending of the outer part such that lateral forces between the inner part the bent outer part are reduced or avoided. This reduces frictional forces under side load conditions between the inner and outer ports compared with using a non-accommodative inner part. The reliability of the instrument is improved. Additionally or alternatively, the amount of side load that the instrument can tolerate before its function is impaired can be significantly increased.

A combination of both aspects of the invention may also be used.

The application of both aspects of the invention to a trocar assembly will now be described, with the understanding that the invention could similarly be applied to other two-component laparoscopic instruments.

In a first embodiment of the first aspect of the invention, the obturator 16 shown in FIG. 1A is provided with lateral compliance by making the obturator of plastic instead of stainless steel. The preferred material for the plastic obturator is a polyetherimid, such as that sold by G.E. Plastics under the brand name Ultem™. A polyetherimid obturator has sufficient axial rigidity to transmit the required axial forces, but has a considerably greater lateral compliance than a stainless steel obturator.

The increased lateral compliance of the obturator enables the trocar to adapt to the bending of the trocar assembly in response to a side load with a relatively small lateral force between the trocar and the trocar tube. This reduces friction between the trocar and the trocar tube. The advantages of reducing friction between the trocar and the trocar tube have already been described. Using a plastic obturator enables the side load required to render the self-shielding mechanism inoperative to be doubled compared with using a stainless steel obturator.

Figure 3A:
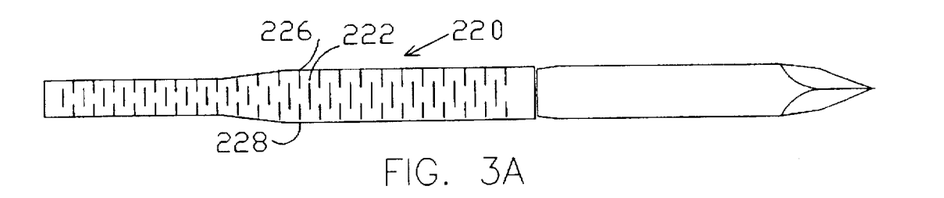
FIG. 3A shows a trocar assembly having an obturator with lateral compliance provided by plural radial slots. Since the rear housing, valve body, and cannula on the embodiments shown in this and the following figures are the same as the rear housing, valve body, and cannula shown in FIG. 1A, these parts have been omitted from this and the following figures for clarity, except where otherwise noted.
Figure 3B:
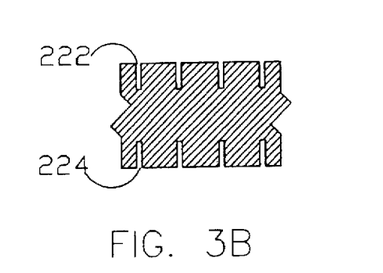
FIG. 3B is a longitudinal cross section of part of the obturator shown in FIG. 3A.
Figure 3C:
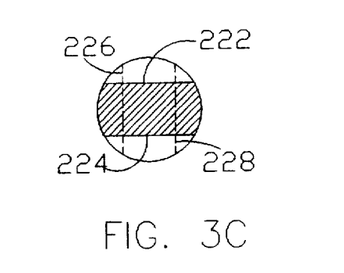
FIG. 3C is a transverse cross section of the obturator shown in FIG. 3A.

A further increase in the lateral compliance of the obturator can be provided by forming radial slots in the obturator. FIGS. 3A through 3C show the slotted obturator 220 in which radial slots such as the slot 222, are formed. The slotted obturator is, again, preferably a plastic molding, preferably of polyetherimid.

The depth of the slots is preferably about one fourth of the diameter of the obturator, and the slots are preferably about 0.03" (0.8 mm) wide. The slots are arranged in diametrically-opposed pairs, such as the pair 222 and 224. FIG. 3C shows how successive pairs of slots are preferably orthogonally offset, with the pair of slots 226 and 228, shown by broken lines, orthogonally offset from the pair of slots 222 and 224. The slots can be formed by cutting them in the obturator, or by molding the obturator with the slots in place.

Figure 4A:
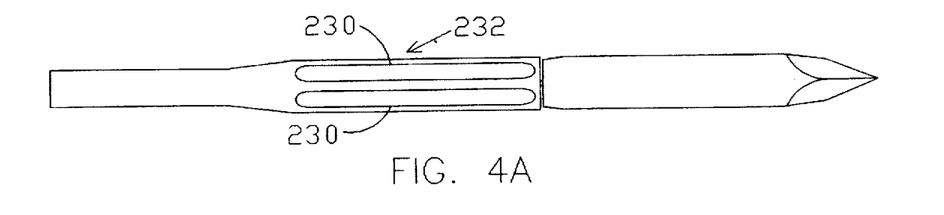
FIG. 4A shows a trocar assembly having an obturator with lateral compliance provided by plural longitudinal flutes.
Figure 4B:
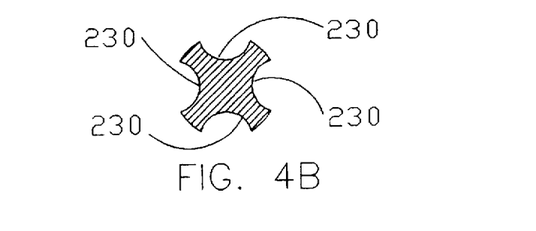
FIG. 4B is transverse cross section of the obturator shown in FIG. 4A.

An alternative way of further increasing the lateral compliance of the obturator is shown in FIGS. 4A and 4B. In this, longitudinal flutes 230 are formed in the fluted obturator 232. The fluted obturator 232 is, again, preferably a plastic molding, preferably of polyetherimid.

The fluted obturator 232 has a lateral compliance comparable with the slotted obturator shown in FIGS. 3A and 3B, but the tool for molding the fluted obturator is considerably simpler than that for molding the slotted obturator.

Figure 5A:
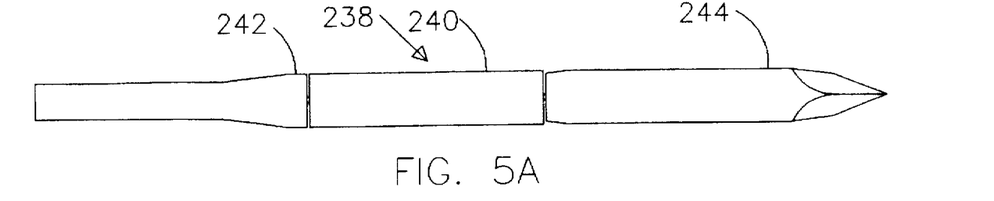
FIG. 5A shows a trocar assembly having an obturator with lateral compliance provided by an elongate flexible section.
Figure 5B:
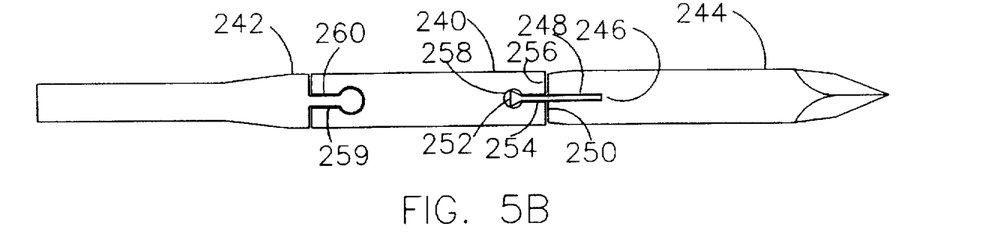
FIG. 5B is a partially cut away view of the trocar assembly shown in FIG. 5A showing a first way of interconnecting the flexible section with the proximal portion of the obturator and the trocar tip.
Figure 5C:
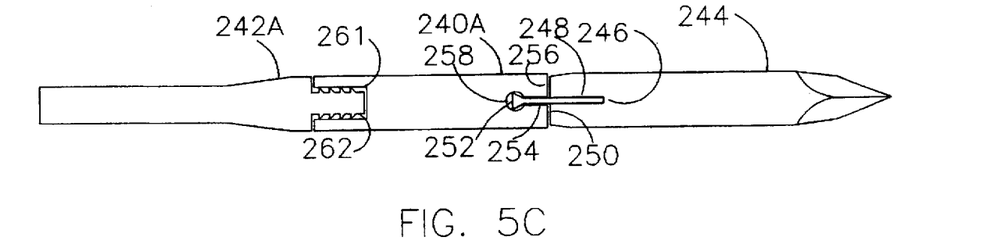
FIG. 5C is a partially cut away view of the trocar assembly shown in FIG. 5A showing a second way of interconnecting the flexible section with the proximal portion of the obturator and the trocar tip.
Figure 5D:
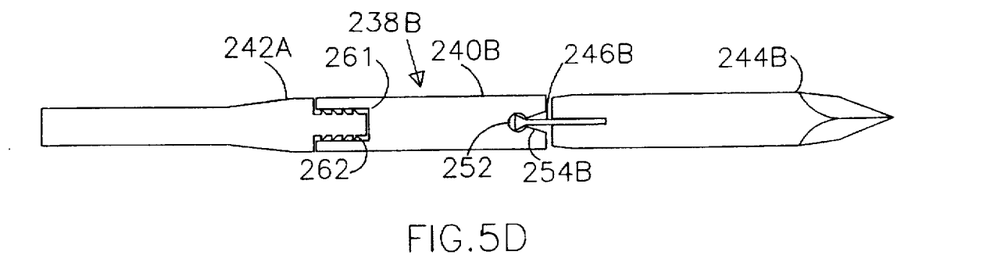
FIG. 5D shows a variation on the trocar assembly shown in FIG. 5A in which additional lateral compliance is provided by an articulated joint between the flexible section and the trocar tip, The view is partially cut away to show a first way of providing the articulated joint.
Figure 5E:
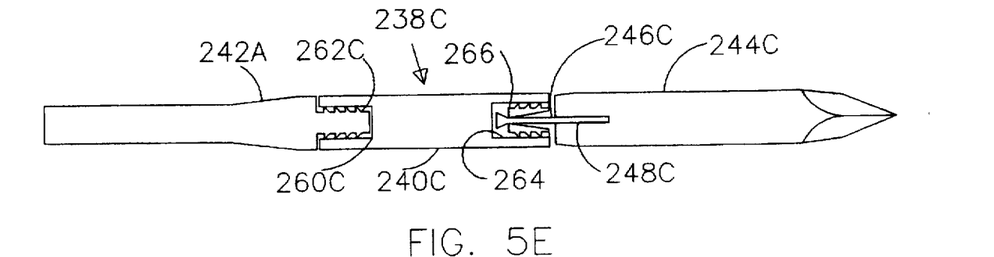
FIG. 5E shows an alternative variation on the trocar assembly shown in FIG. 5A in which additional lateral compliance is provided by an articulated joint between the flexible section and the trocar tip The view is partially cut away to show a second way of providing the articulated joint.

Further alternative embodiments of the first aspect of the invention are shown in FIGS. 5A and 5E. FIG. 5A shows features common to all Of the embodiments shown in FIGS. 5A through 5E. FIG. 5A shows the obturator 238 in which the conventional obturator (e.g., the obturator 16 in FIG. 1) is divided into a compliant distal section 240 and a rigid proximal section 242. The trocar tip 244 is attached to the distal end of the flexible distal section, and the compliant distal section attaches to the rigid proximal section 242. The rigid proximal section is substantially similar to the proximal section of the conventional obturator, and is preferably an polyetherimid molding.

In the embodiments shown in FIGS. 5A through 5C, substantially all the lateral compliance of the obturator is provided by the flexible distal section 240, which is made of a flexible material, such as nylon, or hard rubber. In the embodiments shown in FIGS. 5D and 5E, additional lateral compliance is provided by an articulated joint between the trocar tip 244 and the flexible distal section 240.

In FIGS. 5B and 5C, various ways of interconnecting the flexible distal section 240 of the obturator 238 with the rigid proximal section 242 and the trocar tip 244 are shown. The trocar tip is attached to the flexible distal section 240 using a conventional non-articulated joint. A rigid tube 246 is inserted into an axial bore 248 in the proximal face 250 of the trocar tip, and is attached therein such that it projects from the proximal face. The proximal end 252 of the rigid tube 246 is flared. A relatively deep bore 254, ending in the cavity 258 is molded in the distal face 256 of the flexible distal section 240. The rigid tube is inserted into the bore 254 such that the flared proximal end 252 engages in the cavity 258. The engagement of the flared proximal end of the rigid tube 246 in the cavity 258 axially locates the rigid tube 246, and hence the trocar tip 242, relative to the flexible distal section 242. The trocar tip is free to rotate relative to the flexible distal section 242. The juxtaposition of the rigid tube 246 and the deep bore 254 provides substantially no articulate movement of the trocar tip relative to the flexible distal section, however. Thus, substantially all lateral compliance of the trocar is provided by the flexible distal section 240.

In FIG. 5B, an arrangement similar to that just described is also used to attach the flexible distal section 240 to the rigid proximal section 242. The flared extension 260, which is the equivalent of the rigid tube 242 with the flared proximal end 252 and is preferably molded integrally with the proximal section 242, engages with the contoured bore 259 in the flexible distal section.

In FIG. 5C, the trocar tip 244 is attached to the flexible distal section 240A with an arrangement similar to that shown in FIG. 5B, but a different arrangement is used to attach the flexible distal section to the rigid proximal section 242A. The flexible distal section 240A is molded with a cylindrical bore 261, which is simpler to mold than the contoured bore 259 shown in FIG. 5B. The proximal part 242A of the obturator is molded with a barbed distal extension 262, which is a firm push fit into the cylindrical bore 261 in the flexible distal section 240A. Friction between the barbed distal extension 262 and the cylindrical bore 261 is sufficient to transmit the retraction force to the flexible distal section, and thence to the trocar tip 244, without slipping.

In the embodiments shown in FIGS. 5A though 5C, the flexible distal section 240, 240A provides the obturator with lateral compliance, which enables the obturator to adapt to the bending of the trocar assembly with a relatively small lateral force between the cannula and the trocar. The relatively small lateral force reduces friction between the cannula and the trocar, the advantages of which are set forth above.

In the embodiment shown in FIG. 5D, the lateral compliance is increased compared with that of the embodiments shown in FIGS. 5B and 5C by using an articulated joint between the trocar tip 244 and the distal end of the flexible distal section 240B of the obturator 238B to provide additional lateral compliance. The articulated joint enables the trocar tip to rotate relative to the obturator, and enables the trocar tip to be oriented at an angle relative to the obturator. The articulated joint also transmits the required tensile and compressive axial forces between the obturator and the trocar tip.

To provide an articulated joint between the trocar tip 244 and the flexible distal section 240B, the non-articulated joint shown in FIGS. 5B and 5C is modified. The bore 254B in the distal face of the flexible distal section 240B is tapered instead of cylindrical. The diameter of the bore increases in the distal direction, i.e., towards the trocar tip 244. The angle of the taper determines the maximum angle between the trocar tip 244B and the flexible distal section 240B. If a large maximum angle is required, the depth of the tapered bore 254B may need to be reduced to accommodate the required taper within the diameter of the flexible distal section 240B.

The flexible distal section 240B is attached to the rigid proximal section 242A using, for example, one of the arrangements shown in FIGS. 5B and 5C. An arrangement similar to that shown in FIG. 5C is shown.

An alternative embodiment which is simpler to mold than the embodiment just described is shown in FIGS. 5E and 5E. In this embodiment, the flexible distal section 240C of the obturator 238C is provided at both ends with a cylindrical bore similar to the cylindrical bore 261 shown in FIG. 5C. The cylindrical bore 261 at the proximal end of the flexible distal section accommodates the barbed extension 262 of the rigid proximal section 242, as described above in connection with FIG. 5C.

The cylindrical bore 264 at the distal end of the flexible distal section 240C accommodates the barbed insert 266. The barbed insert, a plastic molding shown in detail in FIG. 5F, includes the tapered bore 268, which determines the maximum angle between the trocar tip 244 and the flexible distal section 240C. Alternatively, a non-barbed insert secured in place by a suitable adhesive could be used.

Figure 5F:
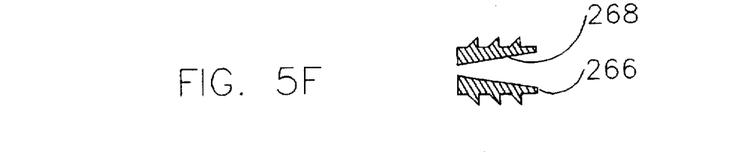
FIG. 5F is a cross sectional view of the insert shown in FIG. 5E.

The barbed insert 266 is attached to the trocar tip 244 by pushing the non-flared end of the rigid tube 246C through the tapered bore 268, starting at the small-diameter end. The non-flared end of the rigid tube 246C is then inserted into the bore 248 in the trocar tip 244, where it is secured in place. The barbed insert 266 is then pressed into the cylindrical bore 264.

In the embodiments shown in FIGS. 5D and 5E, the flexible distal section and the articulated joint between the trocar tip 244 and the flexible distal section 240C together provide the obturator with lateral compliance that enables the trocar to adapt to the bending of the trocar assembly in response to a side load with a relatively small lateral force between the cannula and the trocar. The relatively small lateral force reduces friction between the cannula and the trocar. The advantages of reducing friction between the cannula and the trocar are set forth above.

Figure 6A:
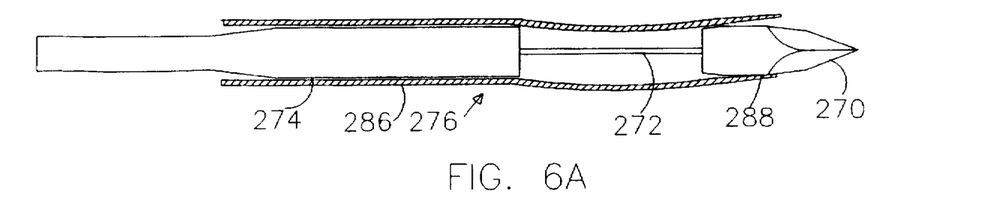
FIG. 6A shows a trocar assembly having a shaped trocar tip that accommodates the lateral displacement of a portion of the cannula resulting from the lengthways bending of the cannula.

A first embodiment of a trocar assembly incorporating the second aspect of the invention is shown in FIG. 6A. In this, the trocar tip is shaped to enable it to accommodate the lateral displacement of a portion of the cannula in response to the side load. Accommodating the laterally displaced portion of the cannula avoids contact, or with reduces contact, between the cannula and the trocar tip. This, in turn, reduces the lateral force, and hence friction, between the cannula and the trocar tip.

FIG. 6A shows the trocar tip 270 attached to the rigid rod 272. The trocar tip 270 is shortened, and the rigid rod 272 is elongated, compared with the trocar tip 244 and the rigid rod 246, respectively, shown in FIG. 5B. The rigid rod 272 is attached to the distal section 274 of the obturator 276 with a non-articulated joint similar to that described above in connection with FIG. 5B. The trocar tip can rotate relative to the obturator 276, but has little lateral compliance.

Figure 6B:
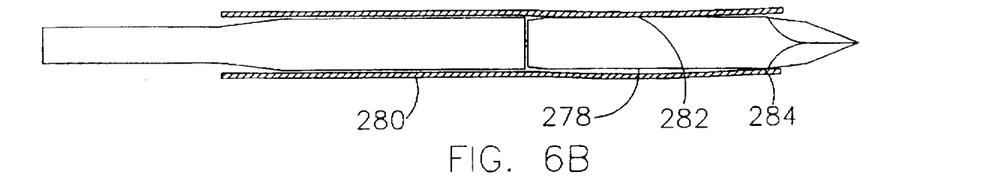
FIG. 6B shows a trocar assembly having a conventional trocar tip in which the lateral displacement of a portion of the cannula resulting from the lengthways bending of the cannula gives rise to a high lateral force, and hence friction, between the cannula and the trocar tip.

FIG. 6B shows a conventional trocar tip 278 in the cannula 280 to which a side load has been applied. The side load causes the cannula to bend, which causes contact, and a lateral force, between the cannula and the conventional trocar tip at the points indicated by the reference numerals 282 and 284.

FIG. 6A shows the shaped trocar tip 270 according to the second aspect of the invention in the cannula 286 to which the same side load has been applied. The side load causes the cannula 286 to bend, but this causes contact, and hence a lateral force, between the cannula and the shaped trocar tip only at the point indicated by the reference numeral 288. There is no contact at a point corresponding to the point indicated by the reference numeral 282 in FIG. 6B because the shape of the trocar tip accommodates the laterally-displaced part of the bent cannula. The reduced contact between the trocar tip and the cannula reduces friction between the cannula and the trocar, the advantages of which are set forth above.

The shaped trocar tip 270 is preferably used in combination with one of the flexible obturator described above.

Figure 7A:
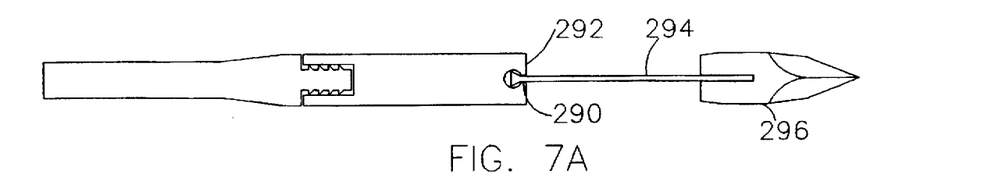
FIG. 7A shows a trocar assembly having a shaped trocar tip that accommodates the lateral displacement of a portion of the cannula resulting from the lengthways bending of the cannula, and additionally having lateral compliance provided by an articulated joint between the relieved trocar tip and the obturator.
Figure 7B:
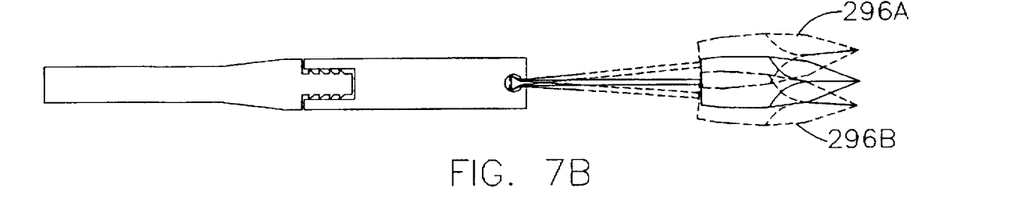
FIG. 7B shows the range of angular movement of the trocar tip provided by the articulated joint.

The capacity of the shaped trocar tip to accommodate bending of the cannula is increased in the arrangement shown in FIG. 7A in which the shaped trocar tip 296 is connected to the obturator using an articulated joint to provide an arrangement with lateral compliance. The articulated joint 291 enables the trocar tip to rotate relative to the obturator, and also enables the trocar tip to be oriented at an angle relative to the obturator, as indicated by the reference numerals 296A and 296B in FIG. 7B. The articulated joint 291 also transmits the required tensile and compressive axial forces between the obturator and the trocar tip.

To provide the articulated joint 291, the non-articulated joint shown in FIG. 5B is modified. Compared with the non-articulated joint, the bore 290 in the distal end of the obturator 292 has a substantially reduced depth, and the diameter of the bore 290 relative to the outside diameter of the elongated rigid tube 294 may also be increased. This arrangement provides the shaped trocar tip 296 with a range of angular movement relative to the obturator 292, which better enables the trocar to accommodate to the shape of the cannula (not shown) when the cannula is bent by a side load. This considerably reduces the lateral force between the cannula and the trocar tip 292. The articulated joint 291 may alternatively be provided using an arrangement similar to those shown in FIGS. 5D or 5E. Again, the arrangement shown in FIG. 7A is preferably combined with one of the flexible obturator described above.

Figure 8:
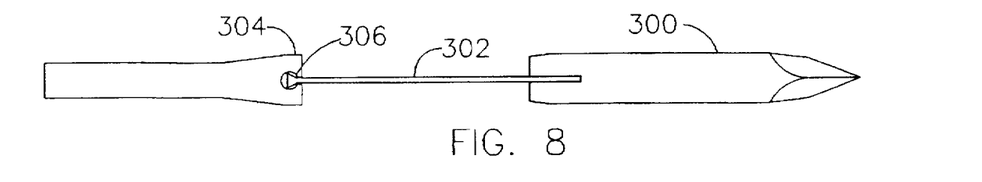
FIG. 8 shows a trocar assembly having a conventional trocar tip and an obturator that includes a shaped section to accommodate the lateral displacement of a portion of the cannula resulting from the lengthways bending of the cannula. The trocar additionally has lateral compliance provided by an articulated joint between the proximal section of the obturator and shaped section of the obturator.

FIG. 8 shown an embodiment in which the conventional obturator is divided into a shaped distal section 302 and a conventional proximal section 304. The shaped distal section extends over most of the length of the obturator, and has a reduced diameter compared to the conventional obturator 16 shown in FIG. 1A. The reduced diameter enables the shaped obturator to accommodate the lateral displacement of a portion of the cannula (not shown) when the cannula is subject to a side load. In this embodiment, the shaped distal section of the obturator is substantially rigid, and is provided by further increasing the length of the rigid tube 302 attached to the trocar tip 300 compared with the length of the conventional rigid tube 246 shown in FIG. 5B. The rigid tube is connected to the proximal section 304 of the obturator by the articulated joint 306, which may be similar to any of the articulated joints shown above. A conventional trocar tip is shown in FIG. 8. A shaped trocar tip similar to that shown in FIG. 7A could alternatively be used if the rigid tube 302 is further extended.

The shaped obturator 302 accommodates the laterally-displaced portion of the cannula (not shown) when the cannula is bent by a side load. This considerably reduces friction between the shaped obturator and the cannula compared with a conventional obturator that substantially fills the cannula. The articulated joint 306 enables the trocar tip 300 to align better with the shape of the cannula when the cannula is bent by a side load, and further reduces friction between the cannula and the trocar tip. The benefits of reducing friction have already set forth above.

The lateral displacement of a portion of the cannula (not shown) in response to a side load can be better accommodated by providing an additional articulated joint (not shown) between the rigid tube 302 and the trocar tip 300. The additional articulated joint can be provided by an arrangement similar to any of the ones already described.

Figure 9A:
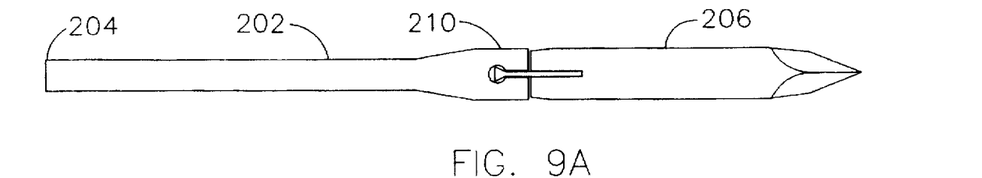
FIG. 9A shows the trocar of the preferred embodiment of a trocar assembly according to the invention. The obturator has a shaped section covering substantially all its length to accommodate the lateral displacement of a portion of the cannula resulting from the lengthways bending of the cannula. The shaped section of the obturator also provides the obturator with lateral compliance.

The preferred embodiment of the invention is shown in FIG. 9A. In this embodiment, the plastic obturator 202 has a diameter that is reduced over most of its length compared with the conventional obturator shown in FIG. 1. The reduced diameter of the obturator 202 provides the obturator both with lateral compliance, and with shaping to accommodate the lateral displacement of a portion of the cannula (not shown) when the cannula is bent by a side load. The obturator 202 is preferably a plastic molding, preferably of polyetherimid.

Compared with a conventional obturator, the diameter of the obturator is reduced along the length of the obturator from the proximal end 204 to within about 10 mm (0.4") of the trocar tip 206. A diameter reduction by between 50% and 70% compared with the diameter of a conventional obturator provides a good range of compromise between axial rigidity on one hand and lateral compliance and accommodating capacity on the other. The preferred obturator shown, which has a diameter reduction of about 65%, has sufficient axial rigidity to transmit the required axial driving force.

A standard trocar tip 206 is attached to the section of increased diameter 210 using, for simplicity, a conventional non-articulated joint, similar to that shown in FIG. 5B.

In the preferred embodiment, the combination of lateral compliance and the ability to accommodate the laterally-displaced portion of the bent cannula (not shown) reduces friction between the trocar and the cannula such that the side load required to render the self-shielding mechanism inoperative is increased by a factor of three compared with the conventional obturator shown in FIG. 1A.

Figure 9B:
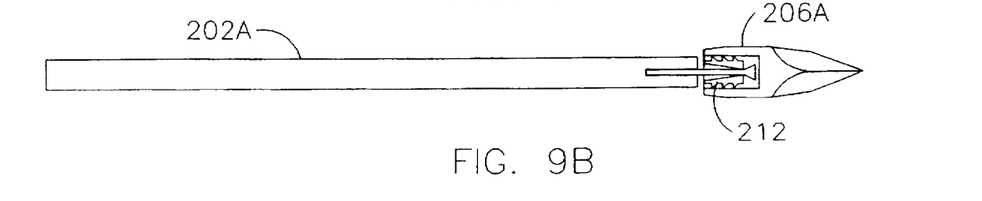
FIG. 9B shows an alternative embodiment of the trocar of the preferred embodiment of the trocar assembly according to the invention. The obturator is shaped over substantially all its length to accommodate the lateral displacement of a portion of the cannula resulting from the lengthways bending of the cannula. The shaping of the obturator also provides the obturator with lateral compliance. Additional lateral compliance is provided by an articulated joint between the obturator and the trocar tip.

If an increase in complexity can be justified, the simple obturator can be modified as shown in FIG. 9B by adding an articulated joint to its distal end. The trocar tip 206A can also be shortened as shown, and the obturator 202A can be correspondingly lengthened. The obturator 202A has a reduced diameter over its entire length. The trocar tip 206A can be attached to the distal end of the obturator 202A using an articulated joint 212 accommodated in the trocar tip.

I claim:

1. A side-load tolerant trocar instrument for use in laparoscopic procedures in a body cavity, the instrument comprising:

an outer part, the outer part being elongate and bending lengthways when a lateral bending force is applied thereto, the outer part, when bent lengthways by the lateral bending force, including a laterally-displaced portion, wherein the outer part is straight in the absence of the lateral bending force; and an inner part, the inner part being an elongate trocar, having a first length, and including a housed portion, the housed portion being part of the first length of the inner part, the housed portion being housed in, and being capable of moving freely axially relative to, the outer part, the housed portion of the inner part having a second length, and being shaped over at least part of the second length to accommodate the laterally-displaced portion of the outer part, wherein the housed portion of the inner part is straight in the absence of the lateral bending force.

2. The instrument of claim 1, wherein:

when the outer part is bent lengthways by the lateral bending force, the laterally-displaced portion of the outer part is displaced towards the inner part; and the housed portion of the inner part is relieved over at least part of the second length to provide a relieved section, the relieved section accommodating the laterally-displaced portion of the outer part.

3. The instrument of claim 2, wherein:

the housed portion of the inner part has a first cross sectional area over a part of the second length excluding the relieved section;

the relieved section has a second cross sectional area; and the second cross sectional area is less than the first cross sectional area.

4. The instrument of claim 3, wherein the housed portion of the inner part includes:

a first elongate section;

a second elongate section, the second elongate section:
being laterally compliant,
having a third length,
including the relieved section, the relieved section occupying substantially all of the third length of the second elongate section, and
being connected to the first elongate section in a substantially linear arrangement.

5. The instrument of claim 4, wherein the distal elongate section is formed of a bending-resistant material, and includes a trocar tip.

6. The instrument of claim 2, wherein the housed portion of the inner part includes:

a first elongate section;

a second elongate section, the second elongate section:
being laterally compliant,
having a third length,
including the relieved section, the relieved section occupying substantially all of the third length of the second elongate section, and
being connected to the first elongate section in a substantially linear arrangement.

7. The instrument of claim 6, wherein the distal elongate section is formed of a bending-resistant material, and includes a trocar tip.

8. A side-load tolerant instrument for use in laparoscopic procedures in a body cavity, the instrument comprising:

an inner part, the inner part being elongate, and having a length, and including a housed portion, the housed portion being part of the length of the inner part; and an outer part, the outer part being elongate, housing the housed portion of the inner part and permitting the housed portion of the inner part to move freely axially relative thereto, the outer part bending lengthways when a lateral external bending force is applied thereto, the outer part exerting a lateral internal bending force on the housed portion of the inner part to bend the housed portion of the inner part lengthways to conform to the lengthways bending of the outer part in response to the lateral external bending force, wherein the outer part is straight in the absence of the lateral external bending force; and wherein the housed portion of the inner part includes an elastic lateral compliance means for reducing the lateral internal bending force required to bend the housed portion of the inner part to conform to the lengthways bending of the outer part in response to the external bending force, wherein the housed portion of the inner part is straight in the absence of the lateral internal bending force.

9. The instrument of claim 8, wherein:

the housed portion of the inner part includes:
a distal elongate section comprising a rigid material,
a proximal elongate section comprising a flexible material, and
a non-articulated joint attaching the distal elongate section to the proximal elongate section in a substantially linear arrangement, and the lateral compliance means includes the proximal elongate section.

10. The instrument of claim 9, wherein:

the distal elongate section has a diameter;

the proximal elongate section has a diameter and a length; and the diameter of the proximal elongate section is less than the diameter of the distal elongate section over at least part of the length of the proximal elongate section.

11. A side-load tolerant trocar assembly, comprising:

a trocar, the trocar being elongate, having a length and including a housed portion, the housed portion being part of the length of the trocar; and a trocar tube, the trocar tube being elongate, housing the housed portion of the trocar, and permitting the housed portion of the trocar to move axially relative thereto, the trocar tube bending lengthways when an external lateral bending force is applied thereto, wherein the trocar tube is straight in the absence of the external lateral bending force, the trocar tube exerting a lateral internal bending force on the housed portion of the trocar to bend the housed portion of trocar lengthways to conform to the lengthways bending of the trocar tube in response to the external lateral bending force; and wherein the housed portion of the trocar includes an elastic lateral compliance means for reducing the lateral internal bending force required to bend the housed portion of the trocar to conform to the lengthways bending of the trocar tube in response to the lateral external bending force, wherein the housed portion of the trocar is straight in the absence of the lateral internal bending force.

12. The trocar assembly of claim 11, wherein:

the housed portion of the trocar includes:
a trocar tip comprising a rigid material, and
an obturator comprising a flexible material, the obturator being connected to the trocar tip in a substantially linear arrangement; and the lateral compliance means comprises the obturator.

13. The trocar assembly of claim 12, wherein:

the trocar tip has a diameter;

the obturator has a diameter and a length; and the diameter of the obturator is less than the diameter of the trocar tip over at least part of the length of the obturator.

14. A side-load tolerant trocar assembly, comprising:

a trocar tube, the trocar tube being elongate and bending lengthways when a lateral bending force is applied thereto, the trocar tube, when bent lengthways by the lateral bending force, including a laterally-displaced portion, wherein the trocar tube is straight in the absence of the lateral bending force; and a trocar, the trocar being elongate and having a first length, and including a housed portion, the housed portion being part of the first length of the trocar, the housed portion being housed in, and being capable of moving freely axially relative to, the trocar tube, the housed portion of the trocar having a second length, and being shaped over at least part of the second length to accommodate the laterally-displaced portion of the trocar tube, wherein the housed portion of the trocar is straight in the absence of the lateral bending force.

15. The trocar assembly of claim 14, wherein:

when the lateral bending force bends the trocar tube, the laterally-displaced portion is displaced laterally towards the trocar; and the housed portion of the trocar is relieved over at least part of the second length to provide a relieved section, the relieved section accommodating the laterally-displaced portion of the trocar tube.

16. The trocar assembly of claim 15, wherein:

the housed portion of the trocar has a first cross sectional area over a part of the second length excluding the relieved section;

the relieved section has a second cross sectional area; and the second cross sectional area is less than the first cross sectional area.

17. The trocar assembly of claim 16, wherein the housed portion of the trocar includes:

a trocar tip;

an obturator, the obturator being laterally compliant, having a third length, and including the relieved section, the relieved section occupying substantially all of the third length of the obturator; and a non-articulated joint connecting the trocar tip to the obturator in a substantially linear arrangement.

18. The trocar assembly of claim 15, wherein the housed portion of the trocar includes:

a trocar tip;

an obturator, the obturator being laterally compliant, having a third length, and including the relieved section, the relieved section occupying substantially all of the third length of the obturator; and a non-articulated joint connecting the trocar tip to the obturator in a substantially linear arrangement.

* * * * *